United States Patent [19]
Holmes et al.

[11] Patent Number: 5,227,300
[45] Date of Patent: Jul. 13, 1993

[54] IDENTIFICATION, CHARACTERIZATION AND METHOD OF PRODUCTION OF A NOVEL MICROBIAL LIPASE

[75] Inventors: Paul E. Holmes, Hamden; Jon A. Kornacki, Wallingford, both of Conn.

[73] Assignee: Olin Corporation, Cheshire, Conn.

[21] Appl. No.: 966,652

[22] Filed: Oct. 23, 1992

Related U.S. Application Data

[63] Continuation-in-part of Ser. No. 749,767, Aug. 26, 1991, Pat. No. 5,168,060, which is a continuation-in-part of Ser. No. 324,062, Mar. 16, 1989, Pat. No. 5,063,160.

[51] Int. Cl.$^5$ ................................................ C12N 9/20
[52] U.S. Cl. ................................................ 435/198; 435/271
[58] Field of Search ........................ 435/198, 271, 874

[56] References Cited

U.S. PATENT DOCUMENTS

| | | | |
|---|---|---|---|
| 3,511,753 | 5/1970 | Prave et al. | 195/62 |
| 3,674,643 | 7/1972 | Aunstrup et al. | 195/62 |
| 4,283,494 | 8/1981 | Kokusho et al. | 435/198 |
| 4,318,818 | 3/1982 | Letton et al. | 252/174.12 |

FOREIGN PATENT DOCUMENTS

| | | |
|---|---|---|
| EP0130064A1 | 2/1985 | European Pat. Off. . |
| EP0331376A2 | 6/1989 | European Pat. Off. . |
| EP0318775A2 | 7/1989 | European Pat. Off. . |
| EP0407225A1 | 9/1991 | European Pat. Off. . |
| 87/00859 | 12/1987 | World Int. Prop. O. . |
| 89/09263 | 5/1989 | World Int. Prop. O. . |
| 91/00908 | 1/1991 | World Int. Prop. O. . |

OTHER PUBLICATIONS

Ralston-Barrett, et. al. (1976) Int. J. Sys. Bateriol. 26(4), 421–426.
Ihara, F., et. al. (1991) J. Biol. Chem. 266(27), 18135–18140.
Wohlfarth, S., et. al. (1992) J. Gen. Micro. 138, 1325–1335.
Chihara-Siomi, M., et. al. (1992) Arc. Biochem. Biophys. 296(2), 505–513.
Jorgensen, S., et. al. (1991) J. Bact. 173(2), 559–567.
Watanabe, N., et. al. (1977) Agric. Biol. Chem. 41(8), 1353–1358.

*Primary Examiner*—Charles L. Patterson, Jr.
*Attorney, Agent, or Firm*—Dale Lynn Carlson

[57] ABSTRACT

A novel lipase from a newly-discovered strain of *Pseudomonas alcaligenes* microorganism having (i) an optimum pH for activity of about $10\pm0.5$; (ii) an optimum temperature for activity of about 45° to 55° C.; (iii) an optimum pH for stability of about $7.0\pm0.5$; (iv) a molecular weight as measured by SDS-PAGE of about $3.0\times10^4$; and (v) chemical stability for at least a 60 day mean half-life in the presence of a 10 percent solution of polyoxyethylene (23) lauryl ether in 25 millimolar aqueous calcium chloride. Also claimed is a biologically pure culture of the microorganism, and a method for the production of the lipase. Also claimed is a lipase characterized by containing an N-terminal amino acid sequence which is Gly-Leu-Phe-Gly-Pro-Ser-Gly-Tyr-Thr-Lys-Thr-Lys-Tyr-Pro-Ile.

4 Claims, 2 Drawing Sheets

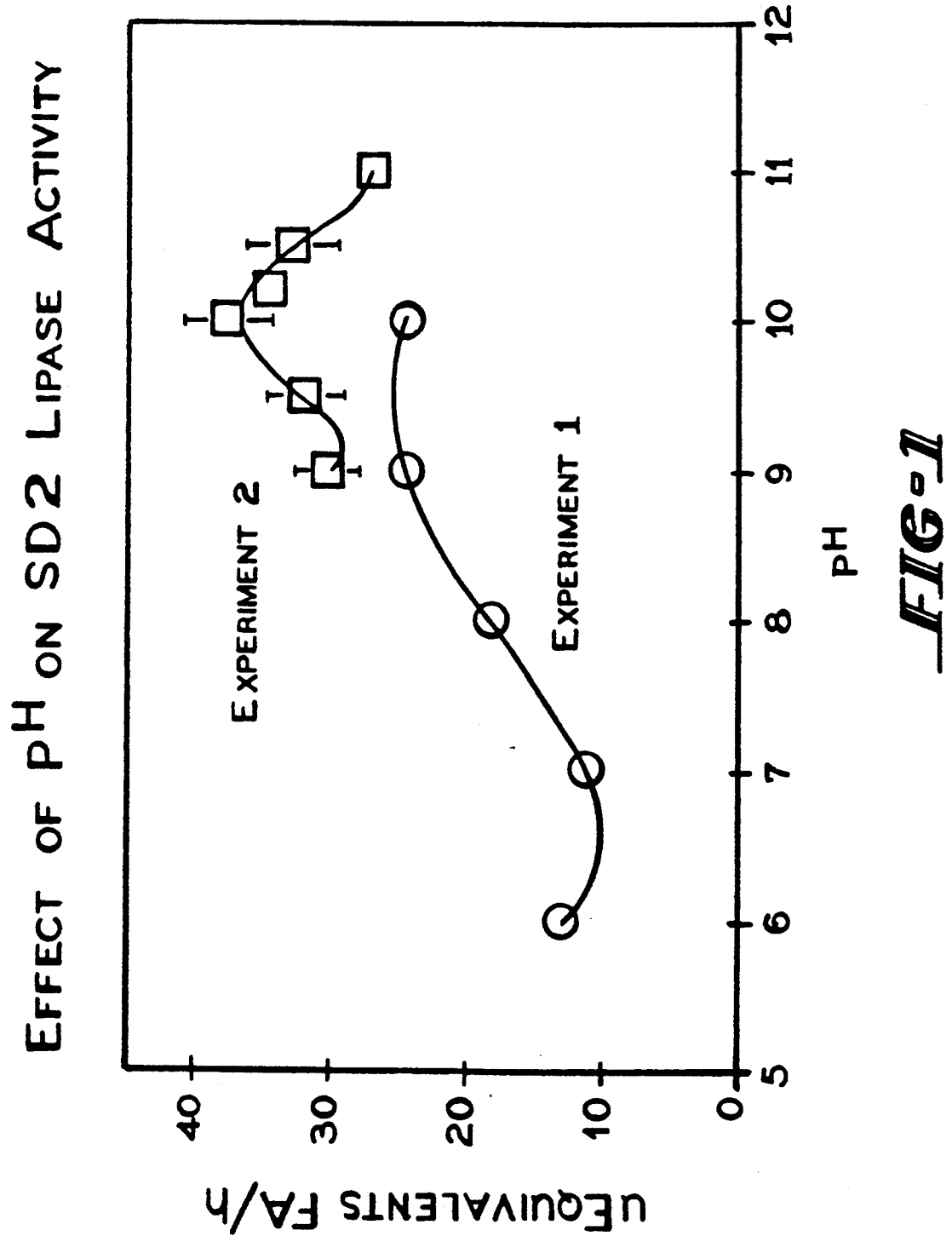

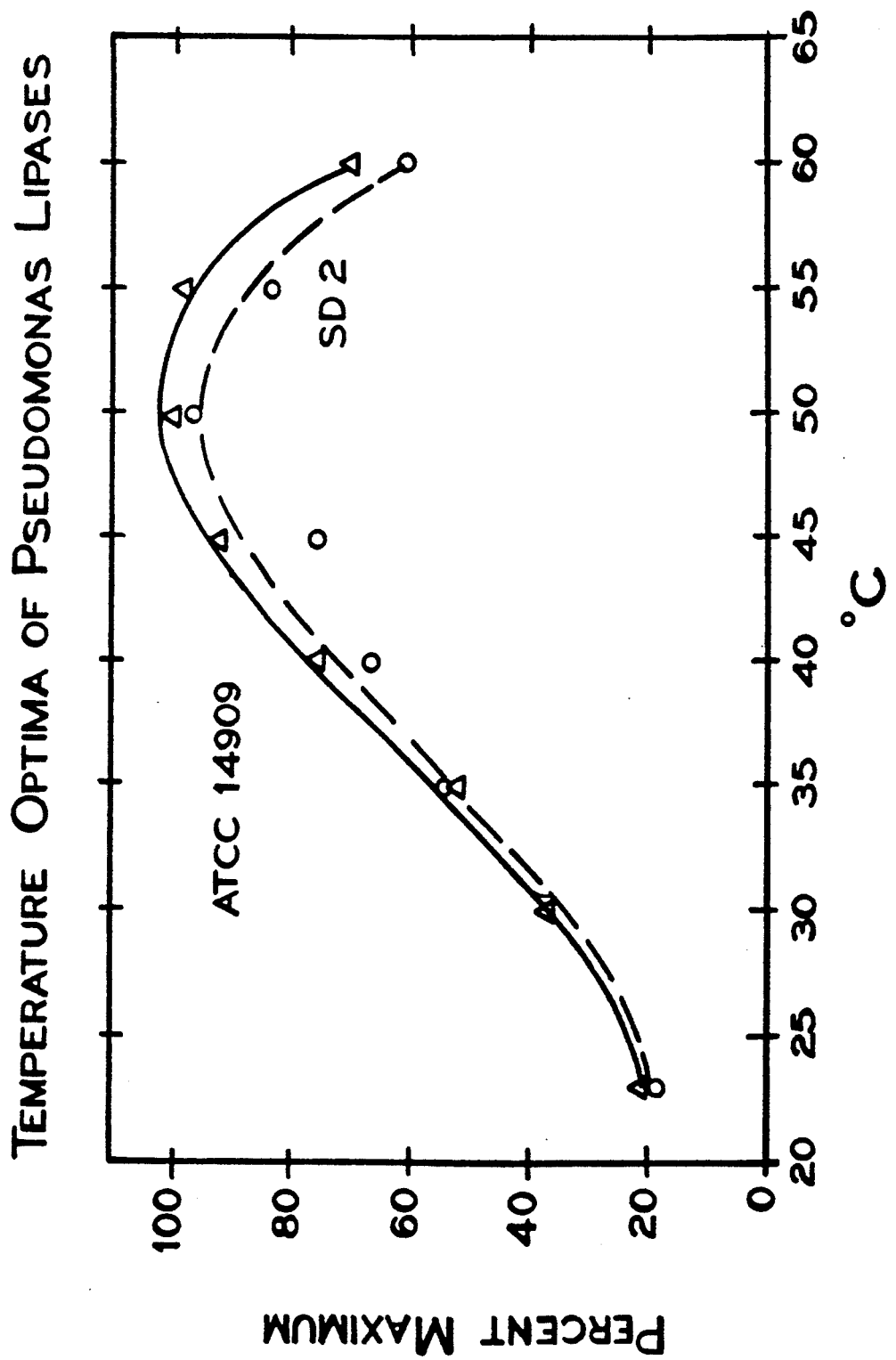

IDENTIFICATION, CHARACTERIZATION AND METHOD OF PRODUCTION OF A NOVEL MICROBIAL LIPASE

This application is a continuation-in-part of patent application Ser. No. 07/749,767 filed Aug. 26, 1991, now U.S. Pat. No. 5,168,060 which is a continuation-in-part of patent application Ser. No. 07/324,062 filed Mar. 16, 1989, now U.S. Pat. No. 5,063,160.

BACKGROUND OF THE INVENTION

This invention herein described relates generally to a biologically-pure culture of a newly-isolated microorganism, a novel microbial lipase produced by this microorganism and its characterization, and methodology for its production. More specifically, the invention relates to the isolation from nature of a new strain of *Pseudomonas alcaligenes* capable of producing a novel lipase under laboratory conditions. Characteristics of this lipase, and methods for its production, are described.

By way of background, the literature is replete with references to the use of microoganisms for the production of commercially important products. Although microscopic unicellular algae and protozoa serve as the source of some commercial products, the most common microorganisms for such purposes are certain types of bacteria and fungi. Commercial products from these microorganisms range from gaseous by-products, to antibiotics, to food additives, and various extracellular or intracellular products such as enzymes and industrial chemicals. Bacterial or fungal isolates are commonly obtained from nature, brought into axenic culture, and used as active ingredients for various degradation treatments or to produce pharmaceuticals or other desirable chemicals.

Various types of microbial enzymes have been reported in the technical and patent literature. For example, the production of proteolytic enzyme preparations from strains of *Bacillus alcalophilus* is described in U.S. Pat. No. 3,674,643. Microbial lipases have been widely reported in the technical literature. For example, lipases have been described in representatives of the following microbial genera: Rhizopus, Fusarium, Helminthosporium, Mucor, Candida, Phycomyces, Aspergillus, Sclerotinia, Pseudomonas, Pheumococcus, Staphylococcus, Mycobacterium, Mycotorula, Chromobacterium, Achromobacterium, Brevibacterium, Corynebacterium, Alcaligenes, and Acinetobacterium. The lipases found among these microbial genera and other microorganisms are quite diverse and typically vary from one another in physical, chemical, and biological properties.

The bacterial genus Pseudomonas consists of a group of aerobic, gram negative, non-spore-forming, rod-shaped bacteria. The organism *P. alcaligenes*, a strain of which is the subject of this invention, is an aerobic pseudomonad which along with *P. pseudoalcaligenes* is included in what is known as the "*Pseudomonas alcaligenes*" group [Ralston-Barrett, E., N.J. Palleroni, and M. Doudoroff, *Inter. J. System. Bacteriol*, 26(4): 421–426 (1976)].

The patent literature is replete with disclosures relating to microbial lipolytic enzymes and their various uses. Examples of such patents and patent applications are: U.S. Pat. Nos. 3,511,753; 4,283,494; and 4,318,818; European Patent Application Nos. 0 214 761, 0 130 069, and 0 130 064; and Patent Cooperation Treaty International Publication No. WO 87/00859. Other types of bacterial enzymes, such as proteases are also disclosed in the patent literature, as illustrated by U.S. Pat. No. 3,674,643. All of these publications are incorporated herein by reference in their entirety.

One of the major commercial uses of microbial lipases is as cleaning compositions, including detergents, to break down lipids. Although a large number of lipolytic enzymes are known in microorganisms, not all such enzymes are suitable for commercial utilization. Such factors as pH range, tolerance of emulsifiers and surfactants, temperature tolerance, storage capability and the like, are important considerations in the selection and development of a commercially useful product.

SUMMARY OF THE INVENTION

In one aspect the present invention relates to a lipase characterized by having (i) an optimum pH for activitiy of about $10\pm0.5$; (ii) an optimum temperature for activity of about 45° to 55° C.; (iii) an optimum pH for stability of about $7.0\pm0.5$; (iv) a molecular weight as measured by SDS-PAGE of about $3.0 \times 10^4$; and (v) chemical stability for at least a 60 day mean half-life in the presence of a 10 percent solution of Polyoxyethylene (23) lauryl ether in 25 millimolar aqueous calcium chloride.

In another aspect, the present invention relates to a lipase characterized by containing an N-terminal amino acid sequence which is Gly-Leu-Phe-Gly-Pro-Ser-Gly-Tyr-Thr-Lys-Thr-Lys-Tyr-Pro-Ile. In a preferred aspect, the lipase has both this N-terminal amino acid sequence and also is characterized by the above-specified pH, temperature, molecular weight and chemical stability properties.

In yet another aspect, the present invention relates to a composition comprising a surfactant and a lipase having an N-terminal amino acid sequence which is Gly-Leu-Phe-Gly-Pro-Ser-Gly-Tyr-Thr-Lys-Thr-Lys-Tyr-Pro-Ile.

These and other aspects will become apparent upon reading the following detailed description of the invention.

BRIEF DESCRIPTION OF THE DRAWINGS

FIG. 1 is a graphic representation of the effect of pH on the enzymatic activity of a preferred lipase obtained from *Pseudomonas alcaligenes* strain SD2, a preferred microorganism of the invention.

FIG. 2 is a graphic representation of the effect of temperature on the enzymatic activity of a preferred lipase of the invention produced from *P. alcaligenes* strain SD2, as compared to a lipase produced from *P. alcaligenes* strain ATCC 14909.

DETAILED DESCRIPTION OF THE INVENTION

The present inventors have now isolated a biologically-pure culture of a previously undescribed strain of *Pseudomonas alcaligenes*. The organism is a natural isolate and has been deposited with the American Type Culture Collection (ATCC), having been assigned the accession number ATCC 53877. This novel strain SD2 was found to produce a novel lipase.

The microorganism of the invention, *P. alcaligenes* strain SD2 was isolated from a shower drain by direct isolation on a Tryptone-Soytone-Olive oil isolation medium. The isolation medium employed is more fully described in Table I below.

TABLE I

| Isolation Medium | |
| --- | --- |
| | Percent by Weight |
| Ammonium sulfate | 0.5 |
| Potassium phosphate, dibasic | 0.05 |
| Magnesium sulfate, heptahydrate | 0.025 |
| Tryptone (Difco) | 1.7 |
| Soytone (Difco) | 0.3 |
| Olive oil | 1.0 |
| Rhodamine B | 0.001 |
| Agar | 1.5 |

The Rhodamine B dye in the isolation medium causes lipase-producing bacterial colonies to fluoresce an orange color when irradiated with long wavelength ultraviolet light (Kouker, G. and K.-E. Jaeger, 1987, *Appl. Environ. Microbiol.*, 53: 211-3). This fluorescence permits the easy identification of lipase-producers. Colonies so identified were purified by restreaking onto similar media. Stock cultures were maintained on Difco TSA slants.

The bacterial isolate of the invention was identified using standard taxonomic procedures from *Bergey's Manual of Systematic Bacteriology* (Williams & Wilkins, Baltimore, 1984). The results of applicable physiological characterization tests of *P. alcaligenes* strain SD2 are presented in Table II and compared with characteristics of *P. alcaligenes* and *P. pseudoalcaligenes* published in Bergey's Manual.

TABLE II

Substrate Utilization of *P. alcaligenes* Strain SD2, *P. alcaligenes*, and *P. pseudoalicaligenes*

| | Strain* | | |
| --- | --- | --- | --- |
| | SD2 | *P. alcaligenes* | *P. pseudoalcaligenes* |
| Fructose | − | − | + |
| L-aspartate | + | − | − |
| L-glutamate | − | + | + |
| D-gluconate | − | − | d |
| L-Histidine | − | d | d |
| Ethanolamine | − | − | + |
| n-Butanol | − | d | + |
| Isobutanol | + | d | − |
| Citrate | − | d | d |
| Betaine | − | − | + |
| Glycerol | − | − | d |
| Sorbitol | − | − | d |
| Itaconate | − | − | d |

Abbreviation:
d (11–80 percent of strain positive);
+ (strain was able to utilize the indicated chemical for growth);
− (strain did not utilize the chemical for growth).
*Data for *P. alcaligenes* and *P. pseudoalcaligenes* are from Bergey's Manual of Systematic Bacteriology (Williams & Wilkins [Baltimore, 1984]).
Compounds utilized by all strains include: DL-lactate, succinate, fumarate, acetate, L-arginine, caprate, and L-malate.
Compounds not utilized by any strain include: D-glucose, L-arabinose, D-mannose, D-mannitol, a-L-rhamnose, D(+)-galactose, D(−)-ribose, m-inositol, L-threonine, m-tartrate, adipate, phenylacetate, nicotinate, sebacate, suberate, benzoate, and pimelate.

This table illustrates nutritional capabilities of the indicated strains and further illustrates their differences. For example, SD2 utilized L-aspartate, while the two other Pseudomonas species did not.

Several lipase-producing strains of *P. pseudoalcaligenes* are disclosed in International Publication No. WO 87/00859 published under the Patent Cooperation Treaty. Table III presents certain morphological and physiological characteristics of *P. alcaligenes* strain SD2, as compared to the characteristics of four strains of *P. pseudoalcaligenes* disclosed in International Publication No. WO 87/00859. Differences between the SD2 strain of the present invention and the other strains are readily apparent.

TABLE III

Characteristics of *P. alcaligenes* Strain SD2 and Selected Lipase-Producing Strains of *P. pseudoalcaligenes*.
(The CBS Strain Accession Numbers Correspond to Those Referenced in International Publication No. WO 87/00859)

| Characteristic | Strain of Invention SD2 | Comparison Strains | | | |
| --- | --- | --- | --- | --- | --- |
| | | CBS 467.85 | CBS 468.85 | CBS 471.85 | CBS 473.85 |
| Cell shape | rod | rod | rod | rod | rod |
| Motility | + | + | + | + | + |
| Spores | − | − | − | − | − |
| Gram Strain | − | − | − | − | − |
| Oxidase | + | + | + | + | + |
| Anaerobic glucose | − | − | − | − | − |
| Aerobic glucose | − | − | − | − | − |
| Aerobic maltose | − | − | − | − | − |
| Aerobic sucrose | − | − | − | − | − |
| Aerobic D-xylose | − | − | − | − | + |
| Arginine dihydrolase | + | + | + | − | + |
| Gelatin hydrolysis | − | − | − | − | − |
| Starch hydrolysis | − | − | − | − | − |
| $NO_3 \rightarrow NO_2$ | + | + | + | + | + |
| $NO_2 \rightarrow N_2$ | + | − | − | − | − |
| Citrate Utilization | − | + | + | + | + |
| Catalase | + | + | + | + | + |
| Growth at 41° C. | + | + | + | + | + |

Strain SD2 of the present invention can be grown in various types of culture media under conditions suitable for growth of pseudomonads. Typically, such media contain assimilable sources of carbon, nitrogen, and various inorganic mineral nutrients. By way of illustration, *P. alcaligenes* strain SD2 was grown in Tryptone Medium having the formulation as shown in Table IV.

TABLE IV

| Culture Medium | |
| --- | --- |
| Ingredient | Percent by Weight |
| Ammonium sulfate | 0.5 |
| Potassium phosphate, dibasic | 0.05 |
| Magnesium sulfate, heptahydrate | 0.025 |
| Tryptone (Difco) | 2.0 |
| BRIJ ® 58 | 1.0 mM |

The lipase of the invention is found in culture media, preferably liquid media, containing *P. alcaligenes* strain SD2. Quantities of this enzyme can be obtained by culturing *P. alcaligenes* strain SD2 in liquid culture and under culture conditions suitable for growth of organisms of this type. For example, an actively growing aliquot of *P. alcaligenes* strain SD2 is suitably used as an innoculum and introduced into Erlenmeyer flasks containing Tryptone medium (C.F. Table IV). Cultures are incubated with shaking for about 16 to 18 hours at a temperature of about 30° C. Following this culture growth period, the bacterial cells are removed by centrifugation or filtration or other suitable techniques. The lipase which is found in the resultant clarified culture liquor is then generally concentrated prior to use. Several methods may be used to concentrate this enzyme, including ultrafiltration as discussed in Example 1.

It is desirable that lipases intended for commercial utilization be stable in the presence of various surfactants commonly found in cleaning product formulations. Advantageously, the lipase of P. alcaligenes strain SD2 was found to be functional in the presence of commercial surfactants such as dodecylbenzene sulfonate and fatty alcohol ethoxylates. In addition, the inclusion of the non-ionic surfactants, such as BRIJ ® 58 [polyoxyethylene (20) cetyl ether] or BRIJ 35 [polyoxyethylene (23) lauryl ether] in liquid growth medium containing P. alcaligenes strain SD2 at a 1-10 mM concentration, preferably 1 mM, increased the yield of the lipase by a factor of two-fold or more in contrast to control cultures without this surfactant.

Regarding the stability of the lipase produced by P. alcaligenes strain SD2, this enzyme loses activity during storage at a rate that is directly proportional to temperature. For example, during accelerated aging tests conducted at a temperature of 37° C. and a pH of 7.0, the lipase of the invention demonstrated a half-life of about 5 days in the absence of surfactants. The addition of calcium, in the form of $CaCl_2$, stabilized the SD2 lipase and increased its half-life to over 80 days at suitable $CaCl_2$ concentrations. The concentration of $CaCl_2$ required to enhance such enzyme longevity is related to the particular lipase formulation. For example, in simple buffered enzyme solutions lacking surfactants, where the buffer is, for example, 50 mM BES [N, N-bis (2-hydroxyethyl)-2-amino-ethanesulfonic acid] at pH 7.0, the addition of 5 mM $CaCl_2$, preferably 10 mM, is sufficient. The optimum concentration of $CaCl_2$ in the presence of preferred surfactants is about 25 mM or more. In formulations of the lipase of P. alcaligenes strain SD2, various surfactants can be used in view of this lipase's stability in the presence of surfactants as illustrated in Table VI below. Examples of preferred surfactants include the nonionic surfactant BRIJ ® 35 [Polyoxyethylene (23) lauryl ether] and the anionic surfactant SANDOPON ® DTC gel. Preferred nonionic surfactants are those having a hydrophobic end containing 12-16 carbon units, and a polyoxyethylene chain size of about 20-23 ethylene oxide units. In general, anionic surfactants of the carboxylated type are preferred and are most compatible with the novel lipase of P. alcaligenes strain SD2.

The following examples further serve to illustrate the invention, but are not intended to be limitative thereof.

EXAMPLE 1

Preparation of Lipase From *Pseudomonas alcaligenes* Strain SD2

The microorganism of the invention, P. alcaligenes SD2, was conveniently grown in the culture medium previously presented in Table IV.

A 50 mL starter culture of P. alcaligenes SD2 in a 250 mL Erlenmeyer flask was grown for about 16 hours at a temperature of 30° C. at 175 rpm on a gyratory shaker. This starter culture was then used to inoculate 8 liters of culture medium which was in turn placed in 4 and 6 L fluted Erlenmeyer flasks such that no individual flask contained more than 25 percent flask capacity as liquid. The culture flasks thus prepared were incubated for 24 hours at a temperature of 30° C. with gyratory shaking at 150 rpm.

Following the culture period, the lipase of the invention is harvested and concentrated by first removing the bacterial cells from the 8 liters of liquid culture by tangential flow filtration using Pharmacia $10^6$ (NMWC) Omega membrane cassettes. The resultant cell-free filtrate was then concentrated by tangential flow ultrafiltration using Pharmacia 30,000 (NMWC) Omega membrane cassettes. Thereafter, the concentrate was diafiltered at 3° C. with about 10 volumes of 50 mM BES, PH 7.0, supplemented with 10 mM $CaCl_2$ in order to eliminate all low molecular weight contaminants (those with molecular weights less than or equal to 30,000), and to change the lipase solvent to one with buffer and stabilizing $CaCl_2$. The yields of enzyme from three separate batch cultures are presented in Table V.

TABLE V

| Yields of Lipase Produced by Cultures of P. alcaligenes Strain SD2 | | |
|---|---|---|
| Batch No. | Units/mL[1] | Total Units |
| 20 | 39.15 | 10,571 |
| 21 | 34.69 | 7,840 |
| 22 | 37.41 | 6,172 |

[1] 1 Unit is the amount of lipase which produces 1 microequivalent of fatty acid from olive oil per minute at 37° C. and at pH 10.

EXAMPLE 2

Determination of Characteristics of the Lipase P. alcaligenes Strain SD2: Molecular Weight, and the Effects of Temperature and pH on Lipolytic Activity Quantities of the lipase of P. alcaligenes strain SD2 were obtained by culturing of the organism in the medium of Table IV, removing the bacterial cells by filtration, concentrating the enzyme by ultrafiltration as already described. Lipolytic activity was assayed using the following standard composition: (i) 2.5 mL substrate [10 percent (w/v) olive oil in 10 percent (w/v) gum arabic]; (ii) 2.0 mL buffer [1.0 M CHES (2[N-cyclohexylamino]-ethane sulfonic acid), pH 10.0]; (iii) enzyme; and (iv) distilled water added to a final volume of 6.0 mL. Enzymatic assays were conducted at a temperature of 37° C. The fatty acids formed during the hydrolytic enzymatic reaction were extracted with an organic solvent and titrated following the procedure described in U.S. Pat. No. 4,283,494.

A quantity of the lipase of the invention was used to determine its molecular weight. The molecular weight of the lipase of P. alcaligenes was found to be about 30,000 using sodium dodecylsulfate-polyacrylamide gel electrophoresis (SDS-PAGE) and comparing the retention time of the lipase with molecular weight calibration standards.

Using the standard procedure for determination of lipolytic activity as described above, the effects of pH as well as temperature on the activity of the lipase of the invention were determined. Results of these experiments are presented in FIGS. 1 and 2.

FIG. 1 shows the effect of PH on activity of the P. alcaligenes strain SD2 lipase. It can be seen that this lipase is active in the pH range from less than pH 6.0 to over pH 11.0, and has an optimum pH of 10.0 (c.f. FIG. 1). FIG. 2 shows the effect of temperature on activity of the P. alcaligenes strain SD2 lipase. Results of these experiments show that the lipase of the invention is active from a temperature of less than 25° C. to over 50° C. and has a preferred temperature for optimum activity of about 50° C. (c.f. FIG. 2).

EXAMPLE 3

Comparison of Characteristics of the Lipase of *P. alcaligenes* Strain SD2 With Other Selected Lipases The lipase of *P. alcaligenes* was contrasted with lipases known to be produced by the type strain of *Pseudomonas alcaligenes* (American Type Culture Collection No. 14909), the Alcaligenes sp. of U.S. Pat. No. 4,283,494 (American Type Culture Collection No. 31372) and the Novo Lipolase TM. Samples of these enzymes were obtained by culturing the respective source organisms and extracting the enzyme from the culture media as described in Example 2 above. Stability of these enzymes in the surfactants BRIJ ® 35 and SANDOPAN ® DTC was determined. In addition to the determination of surfactant stability, the following characteristics of the four microbial lipases were evaluated: optimum pH for enzymatic activity; optimum pH for enzyme stability; optimum temperature for enzymatic activity; and molecular weight. Results of this comparison and associated experiments are presented in Table VI.

TABLE VI

Lipase Characteristics

| Characteristic | SD2 | ATCC 14909[1] | ATCC 31371[2] | NOVO Lipolase TM |
|---|---|---|---|---|
| pH optimum (activity) | 10 | 10 | 9 | 11 |
| pH optimum (stability) | 7 | — | — | — |
| Temperature °C. optimum (activity) | 45-55 | 45-55 | 40-48 | 30-40 |
| Molecular Weight | $3.0 \times 10^4$ | $8.8 \times 10^{4[4]}$ | $30- 40 \times 10^{4[4]}$ | — |
| Surfactant Stability (mean half-life in days): | | | | |
| BRIJ ® 35, 10%[3] | 60 | 5 | — | 11 |
| SANDOPAN ® DTC 20%[3] | 28 | 5 | — | 11 |

[1]*Pseudomonas alcaligenes* type strain
[2]*Alcaligenes* sp. (ref. U.S. Pat. No. 4,283,494)
[3]25 mM CaCl$_2$ added as stabilizer
[4]Determined by gel filtration chromatography It can be seen that the lipase of invention produced by *P. alcaligenes* strain SD2 is novel and differentiable from other known lipases. The SD2 lipase differs from the NOVO Lipolase TM and the lipase of Alcaligenes sp. (ATCC No. 31371) with respect to optimum PH for activity, optimum temperature for activity, surfactant stability, and molecular weight (with respect to ATCC No. 31372; the molecular weight of NOVO Lipolase TM is not known). The lipase of *P. alcaligenes* strain SD2 is comparable to the lipase of the *P. alcaligenes* type strain (ATCC No. 14909) with respect to all characteristics evaluated with the notable exception of surfactant stability. The lipase of the invention produced by *P. alcaligenes* strain SD2 shows exceptionally good stability in certain surfactants tested. The stability of the SD2 lipase in surfactants is unique among the microbial lipases tested.

EXAMPLE 4

Comparison of Characteristics of the Lipase of *P. alcaligenes* Strain SD2 With a Lipase of Kokusho et al An evaluation was made of the characteristics of a lipase as disclosed in U.S. Pat. No. 4,283,494 (to Kokusho et al) as compared to the results obtained for the same characteristics measured for the SD2 lipase of the present invention. Measurements for each characteristic were made by following the procedures of the Kokusho et al '494 patent, except that the assay Protocol for the SD2 lipase employed the buffer described in Example 2 hereinabove and the molecular weight was determined by sodium dodecylsulfate polyacrylamide gel electrophoresis (SDS-PAGE). The results for four characteristics, as compared to the respective results reported in the Kokusho et al '494 patent, are provided in Table VII below.

TABLE VII

Comparison of SD2 Lipase Characteristics vs Kokusho et al

| Characteristic | SD2 | Kokusho |
|---|---|---|
| pH optimum (activity) | $10.0 +- 0.5$ | $9.0 +- 0.5$ |
| Molecular weight | $30 \times 10^3$ | $30–40 \times 10^4$ |
| Activity relative to Olive Oil (100% standard) | | |
| Castor Oil: | 130 | 85 |
| Tricaproin: | 80 | 52 |

The results for the comparison of the characteristics presented in Table VII above show that the SD2 lipase of the present invention is distinctly different from the lipase of Kokusho et al, and the lipolytic activity of the SD2 lipase is improved relative to the lipolytic activity reported for the Kokusho et al lipase.

Determination of N-Terminal Amino Acid Sequence of the Lipase of *P. alcaligenes* Strain SD2 and Comparison With Sequences of Other Known Pseudomonas Lipases Lipase was isolated from culture media of *P. alcaligenes* strain SD2 and concentrated by tangential flow ultrafiltration, as described in Example 1. The lipase was then precipitated by the addition of ammonium sulfate (45% saturation), dissolved in buffer (250 mM ammonium acetate, 10 mM CaCl$_2$), and applied to a Sephacryl S-300 HR column (Pharmacia LKB Biotechnology, Piscataway, NJ). The eluted proteins were fractionated by phase separation in Triton X-114 [3.9% (w/v)] solution (Bordier, C., 1981, *J. Biol. Chem.* 256: 1604–1607). The lipase was recovered in the detergent phase with a purity of >90%, as determined by sodium dodecyl sulfate (SDS)-Polyacrylamide gel electrophoresis. The lipase was further purified for sequencing by electrophoresis on an SDS-polyacrylamide gel, electroblotting onto an Immobilon-P membrane (Millipore, Bedford, MA), staining with Coomassie Brilliant Blue R-250, and excising the section of membrane that contains the lipase band (molecular weight =30,000), as described by LeGendre and Matsudaira (In P.T. Matsudaira (ed.), A practical guide to protein and peptide purification for microsequencing, p. 49–69. Academic Press, Inc., San Diego). The N-terminal amino acid sequence of this SD2 lipase sample was determined by automated sequential Edman degradation at the Yale University Protein and Nucleic Acid Chemistry Facility (New Haven, CT). The results showed that the first 15 N-terminal amino acids of SD2 lipase are Gly-Leu-Phe-Gly-Pro-Ser-Gly-Tyr-Thr-Lys-Thr-Lys-Tyr-Pro-Ile.

The N-terminal amino acid sequence of SD2 lipase was compared to the corresponding sequences of known lipases from the following Pseudomonas species: *P. pseudoalcaligenes* (WO PCT patent application Ser. No. 89/09263 A1), *P. fragi* (EP patent application Ser. No. 0318775 A2), *P. aeruginosa* (Ihara et al., 1991, *J.*

Biol. Chem. 266: 18135-18140; Wohlfarth et al., 1992, J. Gen Microbiol. 138: 1325-1335; Chihara-Siomi et al., 1992, Arch. Biochem. Biophys. 296: 505-513), P. glumae (EP patent application Ser. No. 0407225 A1), P. cepacia DSM 3959 (WO PCT patent application Ser. No. 91/00908 A1; Jorgensen et al., 1991, J. Bacteriol. 173: 559-567), and P. cepacia M-12-33 (EP Patent application Ser. No. 0331376 A2). The sequence comparisons presented in Table VIII show that SD2 lipase is distinctly differenct from all the other Pseudomonas lipases whose sequences have been determined.

a molecular weight as measured by SDS-PAGE of about $3.0 \times 10^4$; and (v) chemical stability for at least a 60 day mean half-life in the presence of a 10 percent solution of polyoxyethylene (23) lauryl ether in 25 millimolar aqueous calcium chloride.

2. The microbial lipase SD2 according to claim 1 which is produced by a microorganism of the genus Pseudomonas having the ability to produce this lipase.

3. A lipase characterized by containing an N-terminal amino acid sequence which is Gly-Leu-Phe-Gly-Pro-Ser-Gly-Tyr-Thr-Lys-Thr-Lys-Tyr-Pro-Ile.

TABLE VIII

Comparison of N-terminal amino acid sequences of lipases from Pseudomonas species

| Species | N-terminal amino acid sequence of lipase[1] | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| P. alcaligenes SD2 | Gly | Leu | Phe | Gly | Pro | Ser | Gly | Tyr | Thr | Lys | Thr | Lys | Tyr | Pro | Ile |
| P. pseudoalcaligenes | Gly | Leu | Phe | Gly | Ser | Thr | Gly | Tyr | Thr | Lys | Thr | Lys | Tyr | Pro | Ile |
| P. fragi | Gly | Leu | Phe | Gly | Phe | Asp | Arg | Ile | Gly | Ser | His | His | Tyr | Phe | His |
| P. aeruginosa | Ser | Thr | Tyr | Thr | Gln | Thr | Lys | Tyr | Pro | Ile | Val | Leu | Ala | His | Gly |
| P. glumae | Ala | Asp | Thr | Tyr | Ala | Ala | Thr | Arg | Tyr | Pro | Val | Ile | Leu | Val | His |
| P. cepacia DSM 3959 | Ala | Ala | Gly | Tyr | Ala | Ala | Thr | Arg | Tyr | Pro | Ile | Ile | Leu | Val | His |
| P. cepacia M-12-33 | Ala | Asp | Asn | Tyr | Ala | Ala | Thr | Arg | Tyr | Pro | Ile | Ile | Leu | Val | His |

[1]All N-terminal amino acid sequences, except that for the P. fragi lipase, are based on amino acid sequence determinations of the purified lipases; the sequence for the P. fragi lipase was predicted from the nucleotide sequence of the gene.

What is claimed is:

1. The microbial lipase SD2 characterized by having (i) an optimum pH for activity of about 10±0.5; (ii) an optimum temperature for activity of about 45° to 55° C.; (iii) an optimum pH for stability of about 7.0±0.5; (iv)

4. A composition comprising a surfactant and a lipase characterized by containing an N-terminal amino acid sequence which is Gly-Leu-Phe-Gly-Pro-Ser-Gly-Tyr-Thr-Lys-Thr-Lys-Tyr-Pro-Ile.

* * * * *